United States Patent [19]

Kim et al.

[11] Patent Number: 5,720,863
[45] Date of Patent: Feb. 24, 1998

[54] PLANAR AIR-TO FUEL RATIO SENSOR AND DRIVING CIRCUIT THEREFOR

[75] Inventors: Ho-in Kim, Yongin-gun; Jong-heun Lee, Seoul; Byung-ki Kim, Kunpo, all of Rep. of Korea

[73] Assignee: Electro-mechanics Co., Ltd., Suwon, Rep. of Korea

[21] Appl. No.: 739,422

[22] Filed: Oct. 29, 1996

[30] Foreign Application Priority Data

Oct. 31, 1995 [KR] Rep. of Korea .................. 95-39058

[51] Int. Cl.$^6$ ................................ G01N 27/407
[52] U.S. Cl. .................. 204/406; 204/412; 204/425; 204/426; 204/429
[58] Field of Search ........................ 204/424, 425, 204/426, 427, 428, 429, 406, 410, 412

[56] References Cited

U.S. PATENT DOCUMENTS

| | | | |
|---|---|---|---|
| 4,658,790 | 4/1987 | Kitahara | 123/440 |
| 4,661,234 | 4/1987 | Takahashi et al. | 204/406 |
| 4,664,773 | 5/1987 | Suzuki et al. | 204/406 |
| 4,718,999 | 1/1988 | Suzuki et al. | 204/406 |
| 4,776,943 | 10/1988 | Kitahara | 204/427 |
| 5,366,610 | 11/1994 | Hirako et al. | 204/406 |

FOREIGN PATENT DOCUMENTS

57-192850  11/1982  Japan .

*Primary Examiner*—Kathryn L. Gorgos
*Assistant Examiner*—William T. Leader
*Attorney, Agent, or Firm*—Burns, Doane, Swecker & Mathis, L.L.P.

[57] ABSTRACT

A planar air-to-fuel (A/F) ratio sensor and a driving circuit therefor are provided. A circuit for driving a planar A/F ratio sensor having a structure wherein an exhaust gas side electrode is shared by a pumping cell and a sensing sell, or a structure wherein an air side electrode is shared by the pumping cell and the sensing cell, is comprised of a comparator for comparing a voltage measured in the sensing cell with a predetermined reference voltage corresponding to the voltage the sensing cell when the pumping cell is within a limit current range to output a voltage which is proportional to the difference between two compared voltages, an integrator for integrating the output of the voltage comparator to output a voltage, an adder for adding a voltage for compensating an electromotive force of the pumping cell to the output voltage of the integrator and an A/F ratio detector for sensing the current flowing through the pumping cell from a voltage output from the adder and applied to the pumping cell to detect an A/F ratio. Therefore, damage to the electrode can be prevented, and the response characteristic between the sensing cell and pumping cell and the accuracy in measuring the A/F ratio can be improved. Also, shift of the current limit region into a region where a voltage $V_p$ is greater than 0 can be compensated by an internal electromotive force of the pumping cell.

4 Claims, 4 Drawing Sheets

PLANAR AIR-TO FUEL RATIO SENSOR AND DRIVING CIRCUIT THEREFOR

BACKGROUND OF THE INVENTION

The present invention relates to a planar air-to-fuel ratio sensor, and more particularly, to a planar air-to-fuel ratio sensor which senses oxygen and reducing gas from an exhaust gas produced as a result of combustion of a fuel mixture, for sensing an air-to-fuel (A/F) ratio of the fuel mixture, and a driving circuit therefor.

In an automobile engine, the output, fuel consumption amount and exhaust gas amount of the engine are changed according to the A/F ratio. Thus, it is desirable to set an optimum A/F ratio according to a traveling condition after sensing the A/F ratio using an A/F ratio sensor.

Various sensors each having a different structure have been realized as A/F ratio sensors. As a representative one of the sensors, there is a stacked-type sensor developed by NGK Insulators, Ltd, shown in FIG. 1. Here, since the stacked-type sensor has a structure that a pumping cell and a sensing cell are separately stacked, the sensor becomes bulky and stacking process is complicated. Also, in an exhaust gas atmosphere of a fuel-rich region, the pumping cell should supply oxygen from the gas of a low oxygen partial pressure to a diffusion chamber, so that an electrode of the pumping cell exposed to the exhaust gas is susceptible to damage.

In order to solve the above problems, Nissan Motor Co., Ltd. has suggested a sensor in U.S. Pat. No. 4,776,943, in which a pumping cell and a sensing cell are both provided on a solid electrolyte as shown in FIG. 2. In this sensor, in contrast with the above sensor shown in FIG. 1, since oxygen is provided from an electrode around the air having a high oxygen partial pressure to an electrode around the exhaust gas in an exhaust gas atmosphere of the fuel-rich region, the exhaust gas side electrode of the pumping cell, can be prevented from being damaged. The pumping cell of this sensor includes one of electrodes which is always exposed to the air, which is different from the NGK sensor having two electrodes of the pumping cell which are always exposed to the exhaust gas.

Due to such a difference, current-versus-voltage characteristics according to the A/F ratio sensed by the A/F ratio sensors shown in FIGS. 1 and 2 are different from each other, as shown in FIGS. 3 and 4. However, since the Nissan sensor shown in FIG. 2 adopts a driving circuit operating with the same principle as that of the driving circuit adopted by the sensor shown in FIG. 1, a problem may occur in actually driving the sensor.

On the other hand, during the operation of the A/F ratio sensor, the pumping cell transfers oxygen in an intended direction via the solid electrolyte to adjust the partial pressure of oxygen in the diffusion chamber, and the sensing cell senses the change in the oxygen partial pressure, caused by the operation of the pumping cell. Thus, gas should be diffused between two electrodes in order for the sensing cell to accurately sense the change in the oxygen partial pressure by its pumping operation. Since the gas diffusion occurs rapidly within a vacant space, the sensing operation can normally be performed. However, it is difficult for the sensing cell to sense the change in the oxygen partial pressure if gas diffusion restricting body is located between two electrodes. Thus, the sensor shown in FIG. 2 should be provided with a diffusion chamber for gas diffusion. However, it is difficult to manufacture a diffusion control barrier having a diffusion chamber.

SUMMARY OF THE INVENTION

In order to solve the above problems, it is an object of the present invention to provide a planar air-to-fuel (A/F) ratio sensor which can prevent damage to electrodes and improve a response characteristic between a sensing cell and a pumping cell, and in which a diffusion control barrier for gas diffusion can easily be manufactured.

It is another object of the present invention to provide a driving circuit for the planar A/F ratio sensor, which compensates the shift of a current limit region to a region where a voltage $V_p$ is greater than 0 in a fuel-rich region by an internal electromotive force of a pumping cell.

To achieve the first object of the present invention, there is provided a planar air-to-fuel (A/F) ratio sensor comprising:

- an oxygen-ion conductive solid electrolyte, having a first surface exposed to atmospheric air and a second surface exposed to a burnt exhaust gas, being opposite to the first surface;
- first, second and third electrodes, the first and second electrodes attached to the first surface of the solid electrolyte and the third electrode attached to the second surface, wherein the first and third electrodes are used as a sensing cell for generating an electromotive force according to oxygen concentration ratio between the first and third electrodes, and the second and third electrodes are used as a pumping cell for migrating oxygen in an intended direction via the solid electrolyte by applying a voltage between the second and third electrodes; and
- a diffusion control barrier located on said third electrode which is on the second surface of the solid electrolyte for controlling diffusion of an exhaust gas to the third electrode.

Here, it is preferable that the diffusion control barrier includes a porous layer located on the third electrode for limiting diffusion of gas. Also, it is preferable that the diffusion control barrier includes a porous layer located on the third electrode for limiting diffusion of gas, and a diffusion blocking layer located on the porous layer for blocking diffusion of gas.

To achieve the second object of the present invention to provide a circuit for driving a planar A/F ratio sensor having a structure that an exhaust gas side electrode is shared by a pumping cell and a sensing cell, or a structure that an air side electrode is shared by the pumping cell and the sensing cell, the driving circuit comprising:

- a comparator for comparing a voltage measured in the sensing cell with a pre-selected reference voltage sensed in the sensing cell within a limit current range to output a voltage which is proportional to the difference between two compared voltages an integrator for integrating the output of the voltage comparator to output a voltage even when output of the voltage comparator is zero;
- an adder adding a voltage for compensating an electromotive force of the pumping cell to the output voltage of the integrator; and
- an A/F ratio detector for sensing the current flowing through the pumping cell from a voltage output from the adder and applied to the pumping cell to detect an A/F ratio.

BRIEF DESCRIPTION OF THE DRAWINGS

The above objects and advantages of the present invention will become more apparent by describing in detail a preferred embodiment thereof with reference to the attached drawings in which.

DETAILED DESCRIPTION OF THE INVENTION

Figure 5:
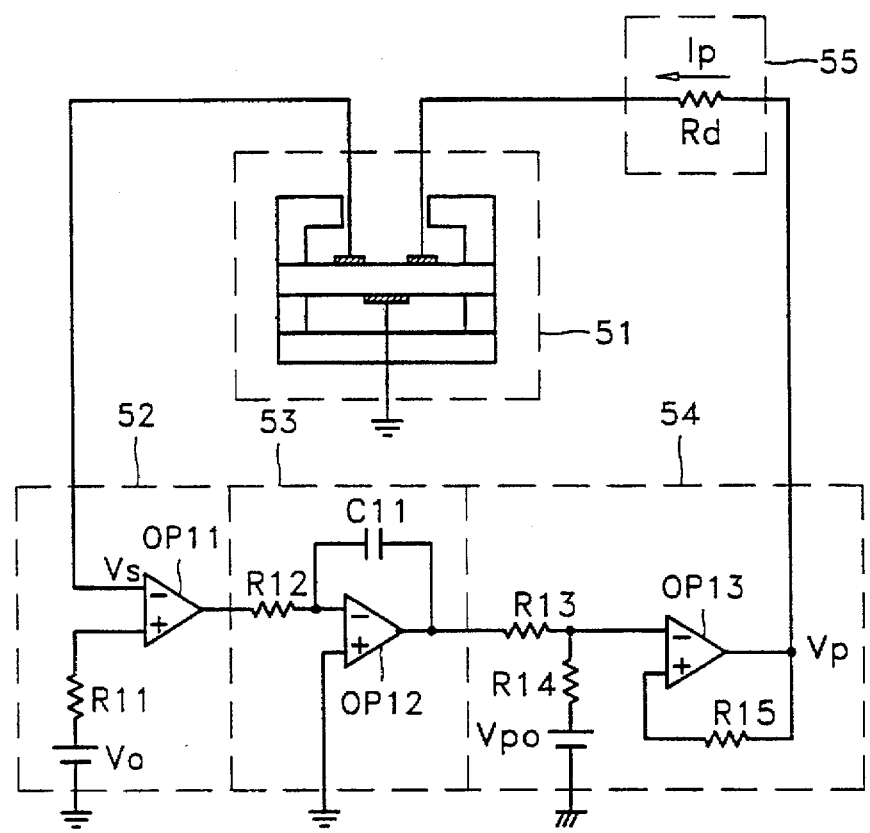
FIG. 5 is a diagram showing a driving circuit according to the present invention for driving the A/F ratio sensor shown in FIG. 2.

As shown in FIG. 5, the driving circuit includes a comparator 52 for comparing a voltage $V_s$ measured in a sensing cell of an air-to-fuel (A/F) ratio sensor 51 with a set voltage $V_O$ (about −450 mV) to generate a voltage which is proportional to the difference between the compared voltages, an integrator 53 for integrating the output voltage of the comparator 52, an adder 54 for adding a pre-selected voltage $V_{po}$ to the output voltage of the integrator 53 to output a voltage $V_p$, and an A/F ratio detector 55, e.g., a resistor Rd, for detecting the A/F ratio from the current depending on the a resistor R11 and a supply source of reference voltage $V_o$. output voltage $V_p$ of the adder 54 applied to a pumping cell. Here, the comparator 52 includes an operation amplifier OP11. The integrator 53 includes a resistor R12, a capacitor C11 and an operation amplifier OP12. The adder 54 includes a resistor R13, a resistor R14, a supply source of a set voltage $V_{po}$, a resistor R15 and an operation amplifier OP13.

Figure 6:
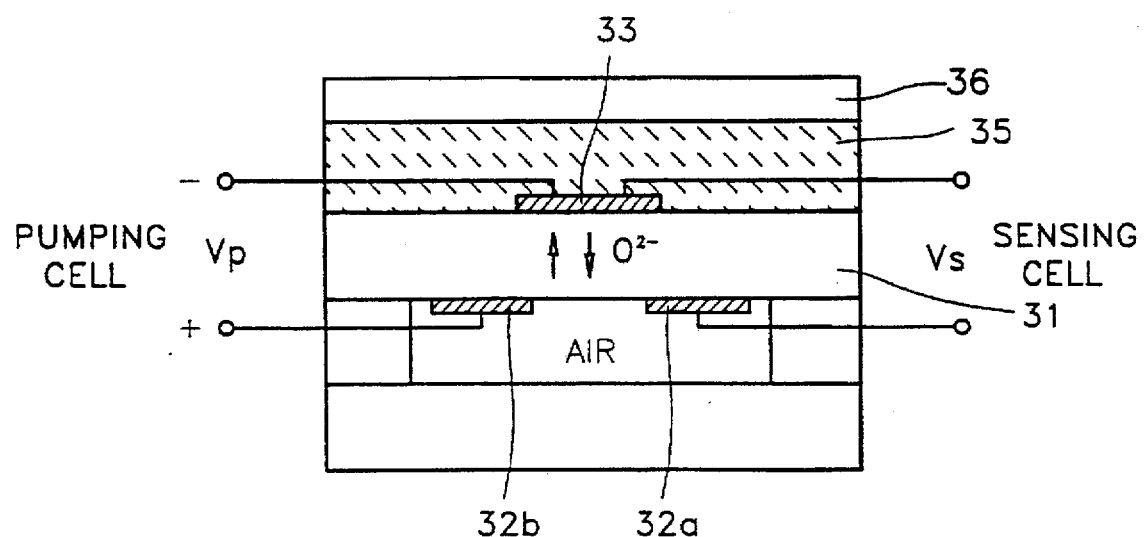
FIG. 6 shows a structure of a planar A/F ratio sensor commonly adopting an exhaust gas side electrode in forming the pumping cell and sensing cell according to the present invention.

FIG. 6 shows a structure of a planar A/F ratio sensor according to the present invention.

The sensor shown in FIG. 6 has an oxygen-ion conductive solid electrolyte 31, and first, second and third electrodes 32a, 32b and 33 are coated on both sides of the solid electrolyte 31. The first and second electrodes 32a and 32b formed on the lower (first) surface of the solid electrolyte 31 are exposed to an atmospheric air via an air duct (not shown) whose one end is blocked. The first electrode 32a is an electrode for a sensing cell which generates an electromotive force according to the difference in the oxygen partial pressure between an exhaust gas and air, and the second electrode 32b is an electrode for a pumping cell which pumps oxygen in an intended direction by applying a voltage thereto. On the other hand, the third electrode 33 formed on the upper (second) surface of the solid electrolyte 31 forms the sensing cell together with the first electrode 32a, and also forms the pumping cell together with the second electrode 32b. Here, since the third electrode 33 of the exhaust gas side is commonly used for forming two cells, the change by the operation of the pumping cell is directly detected by the sensing cell, which does not necessitate a diffusion chamber. Meanwhile, a porous layer 35 for diffusion control may be deposited on the third electrode 33 to be used as a diffusion control barrier.

Also, a diffusion blocking layer 36 for blocking the diffusion of gas may be formed on the porous layer 35.

Figure 7:
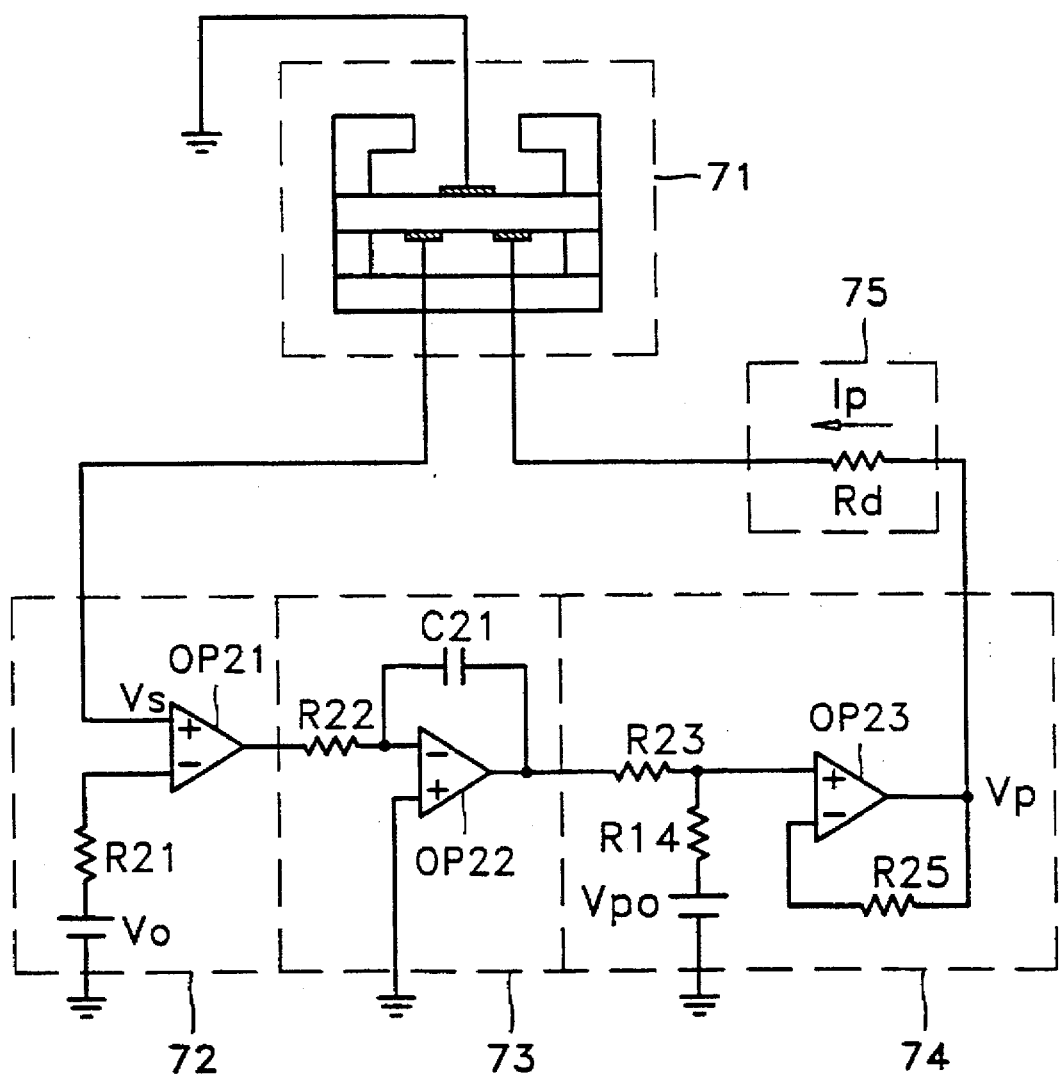
FIG. 7 is a diagram showing a driving circuit for driving the A/F ratio sensor shown in FIG. 6 according to the present invention.

FIG. 7 is a circuit diagram of a driving circuit of the A/F ratio sensor shown in FIG. 6, which is the same as that shown in FIG. 5, except that each inverting and non-inverting input ports of an operation amplifier OP21 which constitutes a comparator 72 and an operation amplifier OP23 which constitutes an adder 74 are contrarily connected, and a set voltage $V_o$ is 450 mV.

Now, the operation of the planar A/F ratio sensor according to the present invention will be described with reference to FIG. 2 and FIGS. 5 to 7.

A mixture ratio of air and fuel gas is called an air-to-fuel (A/F) ratio $\lambda$. Theoretically, $\lambda=1$ when oxygen in the air and fuel gas undergo a complete combustion, $\lambda>1$ when the content of the fuel gas is less than that of oxygen, and $\lambda<1$ when the content of the fuel gas is greater than that of oxygen. Also, in a fuel-lean region ($\lambda>1$), if $\lambda$ becomes larger, the amount of air increases. As a result, the partial pressure of oxygen is increased after combustion, and the partial pressure of a reducing gas such as carbon monoxide (CO) and hydrogen ($H_2$) is decreased to a negligible level. On the contrary, in a fuel-rich region ($\lambda<1$), if $\lambda$ becomes smaller, the partial pressure of oxygen is decreased to a negligible level and the partial pressure of the reducing gas is increased. Thus, the A/F ratio can be detected by measuring the partial pressure of the reducing gas in the fuel-rich region and that of oxygen in the fuel-lean region.

Figure 1:
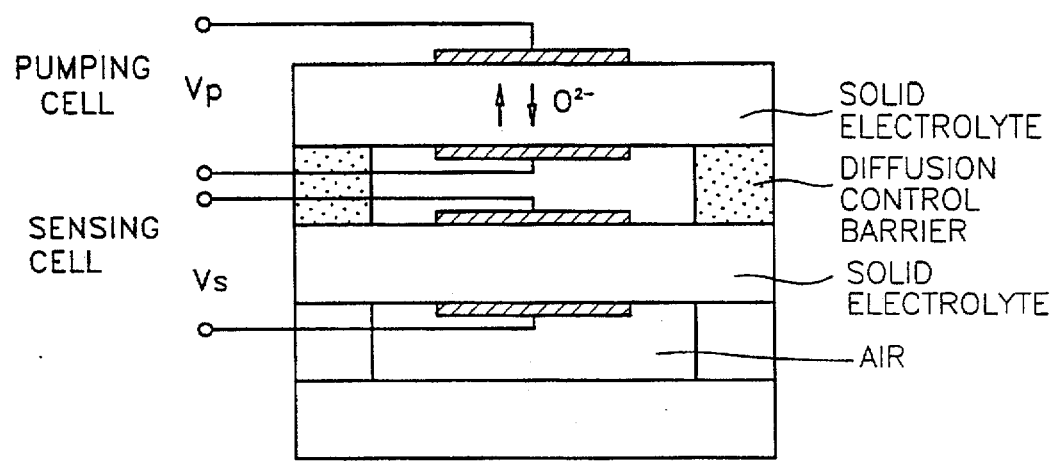
FIG. 1 shows a structure of a conventional an air-to-fuel (A/F) ratio sensor in which a pumping cell and a sensing cell are separately stacked.
Figure 2:
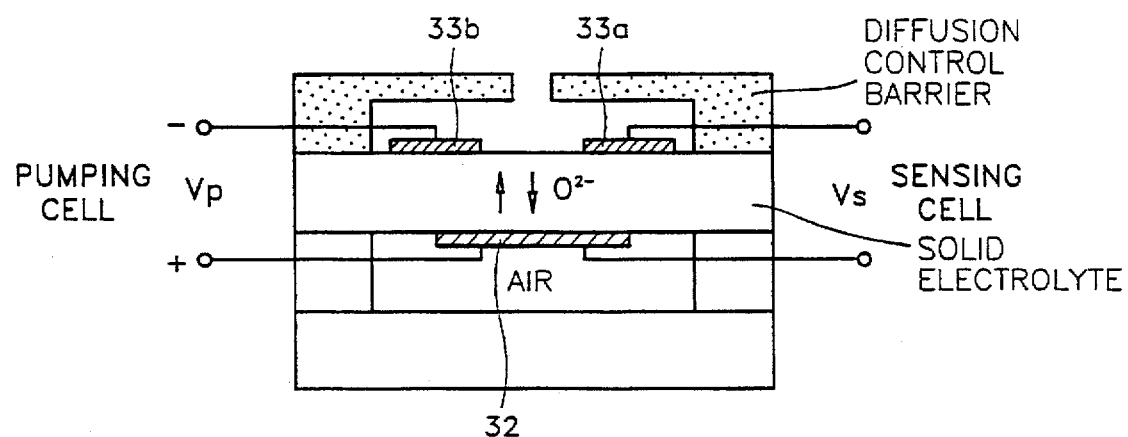
FIG. 2 shows a structure of a conventional A/F ratio sensor proposed by Nissan Motor Co., Ltd.
Figure 3:
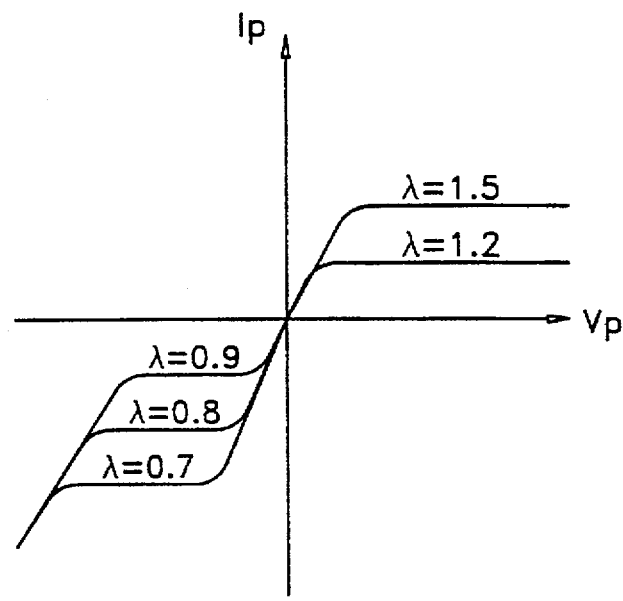
FIG. 3 is a graph showing current-versus-voltage characteristics depending on the A/F ratio of the pumping cell in the A/F ratio sensor shown in FIG. 1.

When a voltage $V_p$ is applied to the pumping cell in the fuel-lean region with the same polarity as shown in FIG. 2, oxygen being around the third electrode 33 moves to the solid electrolyte 31 via the second electrode 32b. Then, the content of oxygen being around the third electrode 33 is lowered, so that oxygen in the exhaust gas is diffused into the third electrode 33 via the diffusion control barrier 35. Here, the amount of diffused oxygen $Q(O_2)$ can be expressed in the following formula (1).

$$Q(O_2)=K(O_2)(P(O_2, \text{exhaust})-P(O_2, \text{electrode})) \quad (1)$$

where $K(O_2)$ represents a diffusion-related coefficient of oxygen, $P(O_2, \text{exhaust})$ represents a partial pressure of oxygen in the exhaust gas, and $P(O_2, \text{electrode})$ represent a partial pressure of oxygen being around the third electrode 33.

The amount of a pumping current $I_p$ flowing in the solid electrolyte 31 is proportional to the diffused oxygen amount in a normal condition, which can be expressed in the following formula (2).

$$I_p=4FQ(O_2) \quad (2)$$

where F represents a Faraday constant.

On the other hand, when the voltage $V_p$ applied to the pumping cell is slightly increased, $P(O_2, \text{electrode})$ around the third electrode 33 can be negligible. On the other hand, the amount of the current flowing in the solid electrolyte 31 is limited by the amount of diffused oxygen induced to the diffusion chamber via a diffusion hole within a proper range of the applied voltage. Here, the limit current $I_p(\text{lim})$ can be expressed in the following formula (3).

$$I_p(\text{lim})=4FK(O_2)P(O_2, \text{exhaust}) \quad (3)$$

On the other hand, since the partial pressure of oxygen is very low in the fuel-rich-region, i.e., about $10^{-20}$ atm, the internal electromotive force of the cell, caused by the difference in oxygen partial pressures, is very high, i.e., about 1V. Thus, even though the voltage $V_p$ which is less than 1V is applied to the fuel-rich region, oxygen in the air is moved toward the diffusion control barrier since the current flow in the solid electrolyte is opposite to that in the fuel-lean region by the internal electromotive force of the cell. Also, a reducing gas such as CO in the exhaust gas reacts with the oxygen having moved from the third electrode 33 via the solid electrolyte to generate carbon dioxide ($CO_2$). Then, the partial pressure of CO around the third electrode 33 is lowered and CO is diffused from the exhaust gas via the diffusion control barrier. Here, the amount of diffused CO Q(CO) can be expressed in the following formula (4).

$$Q(CO)=K(CO)P(CO, \text{exhaust})-P(CO, \text{electrode})) \quad (4)$$

where K(CO) is a diffusion-related coefficient of CO.

In a normal condition, the amount of oxygen passing the solid electrolyte is proportional to the amount of CO entering via the diffusion control barrier. Thus, the flowing current $I_p$ and limit current $I_p(\text{lim})$ can be expressed in the following formulas (5) and (6), respectively.

$$I_p=-2FQ(CO) \quad (5)$$

$$I_p(\text{lim})=-2FK(CO)P(CO, \text{exhaust}) \quad (6)$$

In the formulas (3) and (6), the limit current $I_p(\text{lim})$ is proportional to the partial pressures of oxygen ($O_2$) and carbon monoxide (CO) in the exhaust gas, respectively. Here, hydrogen ($H_2$) can be represented in the same manner as the CO. Thus, the A/F ratio ($\lambda$) can be detected by measuring the limit current $I_p(\text{lim})$. The limit current $I_p(\text{lim})$ is measured when the partial pressures of oxygen and reducing gas such as CO, being around the exhaust gas side electrode are both negligible in the fuel-rich and lean regions. Under this condition, oxygen and reducing gas are balanced in view of their quantities. At this time, the sensing cell adopting an air side electrode as a reference electrode has a voltage $V_s$ ranging from 300 mV to 600 mV. Thus, when controlling the movement of oxygen using the pumping cell to have a voltage $V_s$ of about 300~600 mV, the A/F ratio can be comprehended by the flowing current $I_p$.

Figure 4:
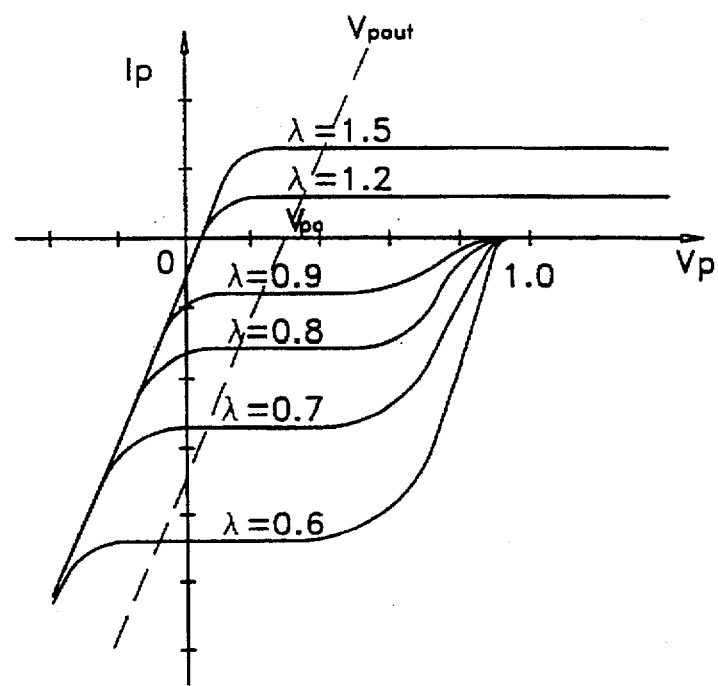
FIG. 4 is a graph showing current-versus-voltage characteristics depending the A/F ratio of the pumping cell in the A/F ratio sensor shown in FIG. 2.

FIG. 4 is a graph showing a current-versus-voltage characteristic of the pumping cell depending on the A/F ratio in the A/F sensor shown in FIG. 2. It is understood that the directions of the current flow are opposite to each other in the fuel-lean and rich regions, and the amount of the limit current increases as the A/F ratio increases. The voltage $V_s$ sensed by the sensing cell within the range of limit current is about 300~600 mV. Thus, if the pumping cell is operated to maintain a certain voltage level in the above range, e.g., 450 mV, the limit current $I_p(\text{lim})$ being proportional to the A/F ratio can be obtained. Also, if the pumping cell does not operate, the level of $V_s$ is about 0~100 mV in the fuel-lean region, about 1V in the fuel-rich region, and about 300~600 mV at a complete combustion point ($\lambda=1$). Thus, if a circuit is devised to have a voltage $V_s$ of about 300~600 mV by operating the pumping cell to remove or supply oxygen from or to the diffusion chamber, a limit current can be always obtained.

A driving circuit according to the present invention for driving the A/F ratio sensor shown in FIG. 2 will be described with reference to FIG. 5.

In FIG. 5, the operation amplifier OP11 of the comparator 52 compares a voltage $V_s$ measured in the sensing cell of the A/F ratio sensor 51, which is applied to the inverting (−) input port, with a reference voltage $V_o$ (−450 mV) applied to the non-inverting (+) input port to output a voltage which is proportional to the difference between two compared voltages. Here, the reference voltage means a voltage sensed by the sensing cell within the range of the limit current.

The operation amplifier OP12 of the integrator 53 integrates the output voltage of the comparator 52, which is applied to the inverting (−) input port, with a predetermined time constant, and outputs the result to the adder 54. Here, even though the voltages $V_s$ and $V_o$ are the same with each other by the operation of the pumping cell, a constant integrated value is output.

The operation amplifier OP13 of the adder 54 adds a predetermined voltage $V_{po}$ to the output voltage of the integrator 53, which is applied to the inverting (−) input port, and then applies the resultant voltage to the pumping cell via the resistor $R_d$. The output voltage $V_p$ of the adder 54 is applied to the pumping cell such that the difference between $V_s$ and $V_o$ is decreased. Here, the added predetermined voltage $V_{po}$ is determined depending on to the current-versus-voltage characteristics of the pumping cell, where the level of the voltage is usually 0.2~0.4V.

As shown in FIG. 4, with the variation in the A/F ratio from the fuel-lean region to the fuel-rich region, the direction of current flow is changed while that of the applied voltage $V_p$ is not changed. On the other hand, since the comparator 52 compares the voltages $V_s$ and $V_o$ based on that $\lambda=1$, the polarity of the output voltage thereof is reversed when the A/F ratio varies from the fuel-lean region to the fuel-rich region. Thus, if the predetermined voltage $V_{po}$ is not added to the output of the comparator 52, the applied voltage $V_p$ deviates from a limit current region while the polarity of the applied voltage is changed from a positive value (+) to a negative value (−). That is, the adder 54 plays an essential role in locate the voltage $V_p$ which is applied to the pumping cell according to the A/F ratio varied from the fuel-lean region to the fuel-rich regions on the limit current region. In FIG. 4, a dashed line representing $V_{pout}$ shows the change in the applied voltage $V_p$ according to the A/F ratio.

The A/F ratio detector 55 detects the current $I_p$ flowing through the pumping cell, and the A/F ratio can be detected by the $I_p$ value.

Next, according to the A/F ratio sensor of the present invention shown in FIG. 6, the exhaust gas side electrode is commonly used for forming the pumping cell and sensing cell while the sensor shown in FIG. 2 uses the air side electrode in common. The basic operation of the sensor is the same as that of the A/F ratio sensor shown in FIG. 2. However, the change in the oxygen partial pressure which is caused by the operation of the pumping cell can be directly detected by the sensing cell since the exhaust gas side electrode is commonly used. Thus, a separate diffusion chamber is not required, so that the diffusion controlling porous layer 35 is deposited on the third electrode 33 to be used as the diffusion control barrier, as shown in FIG. 6. Meanwhile, a diffusion blocking layer (not shown) may be deposited on the porous layer 35 in order to prevent diffusion in a vertical direction and to instead induce diffusion parallel with the diffusion blocking layer. The diffusion blocking layer covering the porous layer 35 functions to protect the weak porous layer 35, thereby increasing the stability as a diffusion control barrier.

On the other hand, the circuit shown in FIG. 7 is for driving the A/F ratio sensor shown in FIG. 5. In the driving circuit of FIG. 7, the operation amplifier OP21 of the comparator 72 compares the voltage $V_s$ measured in the sensing cell of the A/F ratio sensor 71, which is applied to the non-inverting (+) input port, with a reference voltage $V_O$ (450 mV) applied to the inverting (−) input port to output a voltage which is proportional to the difference between two compared voltages.

The operation amplifier OP22 of the integrator 73 integrates the output voltage of the comparator 72, which is applied to the inverting (−) input port, with a predetermined time constant, and outputs the result to the adder 74.

The operation amplifier OP23 of the adder 74 adds a predetermined voltage $V_{po}$ to the output voltage of the integrator 73, which is applied to the non-inverting (+) input port, and then applies the result to the pumping cell via the resistor $R_d$.

As described above, the planar A/F ratio sensor according to the present invention prevents the electrode from being directly exposed to the exhaust gas having a strong reducing property, thereby avoiding the damage of the electrode. Also, since a pumping cell and a sensing cell share an exhaust gas side electrode, the change in the oxygen partial pressure caused by the operation of the pumping cell can directly be sensed by the sensing cell, thereby improving response characteristic of the sensor. Also, since a diffusion control barrier which does not necessitate a diffusion chamber can be applied, the fabricating process of the sensor is simplified.

In addition, in the driving circuit for the planar A/F ratio sensor of the present invention, the predetermined voltage $V_{po}$ is added to the output voltage of the comparator in an adder, so that shift of the current limit region to a region where a voltage $V_p$ applied to the pumping cell is greater than 0 by an inner electromotive force of the pumping cell can be properly compensated. Thus, the applied voltage $V_p$ which can provide a limit current value over the fuel-lean and -rich regions can be output, thereby detecting the A/F ratio very accurately over a wider region.

What is claimed is:

1. A planar air-to-fuel (A/F) ratio sensor comprising:

an oxygen-ion conductive solid electrolyte, having a first surface adapted to be exposed to atmospheric air and a second surface adapted to be exposed to a burnt exhaust gas, being opposite to said first surface;

first, second and third electrodes, said first and second electrodes attached to said first surface of said solid electrolyte and said third electrode attached to said second surface, wherein said first and third electrodes comprise a sensing cell for generating an electromotive force according to an oxygen concentration ratio between said first and third electrodes, and said second and third electrodes comprise a pumping cell for migrating oxygen in an intended direction via said solid electrolyte by applying a voltage between said second and third electrodes; and a diffusion control barrier located on said third electrode which is on said second surface of the solid electrolyte for controlling diffusion of an exhaust gas to said third electrode.

2. A planar A/F ratio sensor as claimed in claim 1, wherein said diffusion control barrier includes a porous layer located on said third electrode for controlling diffusion of gas.

3. A planar A/F ratio sensor as claimed in claim 1, wherein said diffusion control barrier includes a porous layer located on said third electrode for controlling diffusion of gas, and a diffusion blocking layer located on said porous layer for blocking diffusion of gas.

4. A circuit for driving a planar A/F ratio sensor having a structure wherein an exhaust gas side electrode is shared by a pumping cell and a sensing cell, or a structure wherein an air side electrode is shared by said pumping cell and said sensing cell, said driving circuit comprising:

a voltage comparator for comparing a voltage measured in said sensing cell with a pre-selected reference voltage corresponding to the voltage of said sensing cell when said pumping cell is within a limit current range to output a voltage which is proportional to the difference between two compared voltages;

an integrator for integrating the output of said voltage comparator to output a voltage;

an adder for adding a pre-selected voltage for compensating an electromotive force of said pumping cell to the output voltage of said integrator; and an A/F ratio detector for sensing the current flowing through said pumping cell from a voltage output from said adder and applied to said pumping cell to detect an A/F ratio.

* * * * *